United States Patent [19]
Kochinke et al.

[11] Patent Number: 5,338,548
[45] Date of Patent: Aug. 16, 1994

[54] METHOD FOR INCREASING THE STORAGE STABILITY OF PHYSOSTIGMINE

[75] Inventors: Frank Kochinke; Richard W. Baker, both of Fremont, Calif.

[73] Assignee: Pharmetrix Corporation, Menlo Park, Calif.

[21] Appl. No.: 20,009

[22] Filed: Feb. 17, 1993

Related U.S. Application Data

[63] Continuation of Ser. No. 487,546, Mar. 2, 1990, abandoned.

[51] Int. Cl.$^5$ ............................................. A61F 13/00
[52] U.S. Cl. ......................................... 424/449; 424/448
[58] Field of Search ................................. 424/448, 449

[56] References Cited

U.S. PATENT DOCUMENTS

| | | | |
|---|---|---|---|
| 4,559,054 | 12/1985 | Bruck | 424/449 |
| 4,765,985 | 8/1988 | Leeson et al. | 424/449 |
| 4,788,063 | 11/1988 | Fisher | 424/449 |
| 4,837,025 | 6/1989 | Guillemet et al. | 424/486 |
| 4,839,174 | 6/1989 | Baker et al. | 424/486 |
| 4,867,982 | 9/1989 | Campbell et al. | 424/449 |
| 4,869,909 | 9/1989 | Takahashi et al. | 424/486 |
| 4,880,690 | 11/1989 | Szycher et al. | 424/486 |
| 4,908,213 | 3/1990 | Govil et al. | 424/449 |
| 4,911,707 | 3/1990 | Heiber et al. | 424/449 |
| 5,064,654 | 11/1991 | Berner | 424/448 |
| 5,089,267 | 2/1992 | Hille et al. | 424/449 |

Primary Examiner—Gabrielle Phelan
Attorney, Agent, or Firm—Townsend and Townsend Khourie and Crew

[57] ABSTRACT

This patent relates a method for increasing the storage stability of physostigmine free base and physostigmine analogs by incorporating the free base into a polymer matrix. Chemically compatible enhancers and adjuvants do not interfere with the stabilization of the free bases.

6 Claims, 2 Drawing Sheets

METHOD FOR INCREASING THE STORAGE STABILITY OF PHYSOSTIGMINE

This is a continuation of application Ser. No. 07/487,546 filed 2 Mar. 1990 now abandoned.

FIELD OF THE INVENTION

This invention is directed to devices and methods for the percutaneous administration of physostigmine and its closely related chemical analogs.

BACKGROUND OF THE INVENTION

Acetylcholine (ACh), an essential neurotransmitter, occurs both within the brain and in the peripheral parasympathetic nervous system. Impulses conducted along muscle fibers or axons depend upon the formation of ACh at the synaptic junction for transmission of the impulse to other fibers or axons. Acetylcholine's function as a transmitter is terminated (switched off) when it is converted to choline and acetic acid by the enzyme acetylcholinesterase (AChE). Modern biophysical methods have revealed that the amount of time consumed for the process of conversion of ACh to choline and acetic acid is less than one thousandth of a second. Drugs that have the ability to inhibit or inactivate AChE are called anticholinesterases or AChE inhibitors. As a result of AChE inhibition, acetylcholine accumulates in the synaptic cleft; since ACh is not switched off, impulses are transmitted to the affected site for a longer period of time than would otherwise occur and results in a stronger or more prolonged neuromuscular action. Since these ACh parasympathetic synapses are widely distributed in the brain and peripheral nervous syslem, it is not surprising that AChE inhibitors produce a wide variety of effects on both the brain and body.

Physostigmine is one of the naturally occurring acetylcholinesterase inhibitorsl It has been isolated from the dry, ripe seed of the calabar or ordeal bean, a perennial plant (Physostigma venenosum), found in the Calabar region of Nigeria, West Africa. Also called Esre nut, chop nut or bean of Etu Esre, calabar bean was used as an ordeal poison. As a test of guilt, the suspect was forced to ingest a quantity of calabar beans. If he died, his guilt was proved. If the accused was confident of his innocence and ate the beans rapidly, the chances were high that he would regurgitate the beans and survive the ordeal. (It is reported that proof of guilt or innocence was not always left to chance. Apparently, a placebo was given to those prejudged to be innocent by the tribal elders in order to avoid any potential miscarriages of tribal justice), see *Plants in the Development on Modern Medicine,* Swain, T. ed., Harvard University Press, p. 303–360 (1972). Physostigmine, isolated from the calabar bean, was introduced into medicine for the treatment of wide angle glaucoma in 1877 by Laqueur.

Glaucoma is a disease characterized by an increase in intraocular pressure that, if sufficiently high and persistent, can lead to damage to the optic disc and result in permanent blindness. Wide angle glaucoma, or chronic, simple glaucoma occurs when the meshwork of pores of small diameter involved in the outflow of the aqueous humor lose their tone. Wide angle glaucoma has a gradual, insidious onset and is generally not amenable to surgical improvement. In this type of glaucoma, control of ocular pressure is only possible with continuous and permanent drug therapy.

Myasthenia gravis is a neuromuscular disease characterized by weakness and marked fatigability of skeletal muscles. Its clinical manifestations were described before the turn of the century, but it was not until the early 1930s that physostigmine was used in the management of this disease. The observation that physostigmine gave rise to increased strength of muscular contraction and the similarity between the symptoms of myasthenia gravis and curare poisoning in animals, suggested that physostigmine, an agent then known to antagonize curare, might be of therapeutic value for this disease. This observation led to the use of physostigmine in the treatment of myasthenia gravis.

Tardive dyskinesia is a disease characterized by abnormal, involuntary movements, usually of oral and facial musculature but often involving the trunk and extremities. Typical of oral and facial movements are puffing of the cheeks, grimacing, protrusion and licking of the tongue, and incessant blinking of the eyes. The abnormal movements are rhythmic and repetitive and may interfere with speech, salivation, chewing, and swallowing. Patients, many times, are not aware of the symptoms. Tardive dyskinesia is usually irreversible and considered to be incurable at the present time. Therefore, prevention of the manifestations of this disease is considered to be the only known effective method for dealing with the problem. Tardive dyskinesia is most frequently found in geriatric patients who have been taking neuroleptic drugs. All neuroleptic drugs may cause tardive dyskinesia. However, the low-dose, high potency drugs which produce the greatest degree of blockage, and thus a greater degree of pyramidal side effects are the most likely to cause tardive dyskinesia. Such high potency drugs include the phenothiazines, the thioxanthenes, the butyrophenones, the benxodiazepines and the dihydroindolones. In recent years, the greater use of psychotropic drugs has aggravated the incidence of tardive dyskinesia. The increasing use of neuroleptic drugs in geriatric care facilities has resulted in dramatic increase in the incidence of tardive dyskinesia. See Geriatrics, Volume 34, Number 7, pages 59–66, July 1979, by Harcourt Brace Jovanovich, Inc. An investigation in the use of anticholinergic drugs reported in American Journal of Psychiatry, Volume 134, Number 7, July 1979, pages 769–774 indicates that the use of physostigmind and choline have positive therapeutic effects on tardive dyskinesia. Although the data presented is not unequivocal, tests have shown that physostigmine injections reduce tardive dyskinesia in from 20% to 80% of the patients suffering from tardive dyskinesia. Continuous and permanent drug therapy is necessary to control tardive dyskinesia.

Senile dementia of the Alzheimer's type (SDAT) is a progressive, incurable, and irreversible disease characterized by long term memory impairment. Studies in humans and animals have implicated cholinergic processes in memory functioning. Investigations with anticholinergics and cholinomimetics indicate that fluctuations in cholinergic activity can profoundly affect storage and retrieval of information in memory. Davis, et al. in a study by reported in Science, Volume 201, p.272 (1978) concluded that physostigmine significantly enhanced storage of information into long-term memory. This study moreover indicates that retrieval of information from long-term memory was also improved by physostigmine therapy.

Treatment of tardive dyskinesia, wide angle glaucoma, SDAT, and the like, by injection of physostigmine is not practical therapy. Physostigmine exhibits a short half-life (about 1 to 2 hours) due to rapid metabolism following systemic administration. Thus, treatment would require injections of physostigmine every 30 minutes to 1 hour at a minimum, to maintain efficacious blood levels. Additionally, physostigmine has a narrow therapeutic window which necessitates constant patient monitoring for safety in order to avoid side effects which limit physostigmine's systemic use. Recently, physostigmine has been formulated into tablets for oral dosage. Determination of drug blood levels for multiple oral doses show typical variations in blood concentration ranging from a maxima above the required level (and possibly in the toxic range) to a minima which may be below the effective dose. The dysfunctions mentioned above, as well as many others, are more prevalent among the elderly. This population group endures more memory impairment and physical disability than other age groups and consistent therapy is necessarily more difficult to attain. Percutaneous administration of physostigmine has many advantages over systemic therapy. It is well known that patient compliance is improved where therapy can be attained with fewer numbers of drug applications within a twenty-four hour period. Transdermal administration offers the possibility that application of an appropriate device need occur but once in a twenty four hour period. Therapy can be terminated by removal of the transdermal device. Stable blood levels can be obtained using dose-controlled devices, thus limiting the toxic side effects caused by overdosing and the lack of effect due to underdosing. Pharmacologically active agents with short metabolic lifetimes are particularly suited to transdermal methods of drug delivery.

The literature is filled with descriptions of transdermal devices for the slow or sustained or controlled release of medicaments. These devices may take the form of monolithic reservoir devices, osmotically driven devices, membrane controlled devices, enhancer controlled devices, microencapsulated drugs, bioerodable devices and almost every conceivable combination of the above. For a general review of the art see, "Controlled Release of Biologically Active Agents", R. W. Baker, John Wiley and Sons, 1987. All of the dosing methods and devices used in drug therapy carry an implicit and many times unstated assumption, that the drug released has not been altered upon storage in any way to significantly decrease its efficacy or accumulate undesirable or unacceptable break-down products. It is well known that most free base alkaloids are not stable against air oxidation, actinic radiation, heat etc. Physostigmine free base is a particularly labile compound because its two basic tertiary amine groups facilitate hydrolysis of its phenolic carbanilide group. Once hydrolysis has taken place, contact with atmospheric oxygen will rapidly oxidize the phenolic hydroxyl group to the highly colored ortho-quinone, rubreserine, see, *Studies on Physostigmine and related substances, IV Chemical Studies on Physostigmine Breakdown Products and Related Epinephrine Derivatives*, S. Ellis, J. Pharmacol. Exp. Ther., 79 (1943) pp 364–372. See Reaction I. Consequently, chemicals of this class are commonly stored and administered as their salts. For example, because physostigmine is difficult to store as its free base, the salicylate salt is sold as a commercial preparation with the admonition that solutions should be kept well closed in light-resistant, alkali-free glass containers and used within a week of opening. The practitioner is cautioned to discard the preparation if it is discolored. In almost all cases, the free base is preferred for transdermal permeation because the free base will quickly cross the stratum corneum skin barrier while the salt form is poorly, if at all, transported and absorbed. Many approaches have been tried to solve this conflicting problem of storage vs permeability. For example, Banerje, in U.S. Pat. No. 4,692,462, binds the free base of drug on an ion exchange resin and relies upon the absorption of an equilibrium concentration of the free base form of the drug by the skin for utility. Lee and Yum in U.S. Pat. No. 4,781,924, store a variety of basic drugs in their salt form in combination with a dry basic compound. Upon moisture absorption, a solution is formed which permits the reaction between the alkaline compound and the salt form of the organic base, liberating the free base. The free base migrates through the device to the skin surface where it rapidly permeates the skin barrier. These inventions serve to illustrate the lengths to which those skilled in the art have gone in order to contain the therapeutic agent in its stable form as the salt, and administer the drug in its most biologically useful form, the free base. The foregoing discussion illustrates the need and value of a device or method that contains the target drug in its most active and bioavailable form (free base) while maintaining adequate storage stability.

Conventional wisdom has indicated that effective protection against the deleterious effects of oxygen and moisture could not be achieved by employing the various polymers as monolithic matrices for sensitive drugs. Diffusion of atmospheric oxygen and water vapor are thought to be so high that drugs sensitive to hydrolysis or oxidation, stored for any significant length of time under ambidnt conditions, would be quickly converted to the expected degradation products. Comequently, past efforts toward dealing with the problem of drug instability have been dedicated to converting the target drug into a chemical form that has adequate storage stability.

OBJECTS OF THE INVENTION

It is the object of this invention to disclose a novel means for increasing the storage lifetime of drugs.

It is another object of this invention to disclose a novel means for increasing the storage lifetime of physostigmine free base and its closely related analogs.

It is another object of this invention to disclose novel transdermal devices for the release of physostigmine free base and its closely related analogs.

It is another object of this invention to disclose devices and methods for controlled release of compounds effective in the treatment of memory impairment, glaucoma, tardive dyskinesia and myasthenia gravis.

It is another object of this invention to provide a means for treatment of disorders resulting from a deficiency of acetylcholine.

It is a further object of this invention to provide a means for symptomatic treatment of disorders resulting from a deficiency of acetylcholine.

Further objects of the invention will be apparent from the description of the invention to those skilled in the art.

SUMMARY OF THE INVENTION

The present invention stabilizes compounds containing chemically labile functional groups, such as physostigmine free base, by incorporating them into a monolithic polymer matrix.

The effective compounds include physostigmine free base and physostigmine derivatives. Physostigmine free base and physostigmine free base derivatives may be represented by formula I as follows:

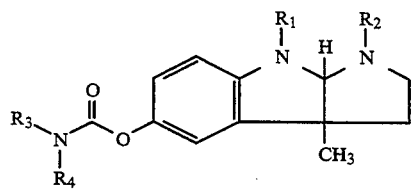

In formula I, R1, R2, R3 and R4 independently represent H or lower alkyl groups.

Chemically similar functional groups are defined as hydrolytically, oxidatively or hydrolytically and oxidatively unstable moieties.

"Monolith" as used herein means a single-phase combination of chemical and polymeric carrier.

DETAILED DESCRIPTION OF THE INVENTION

Figure 1A:
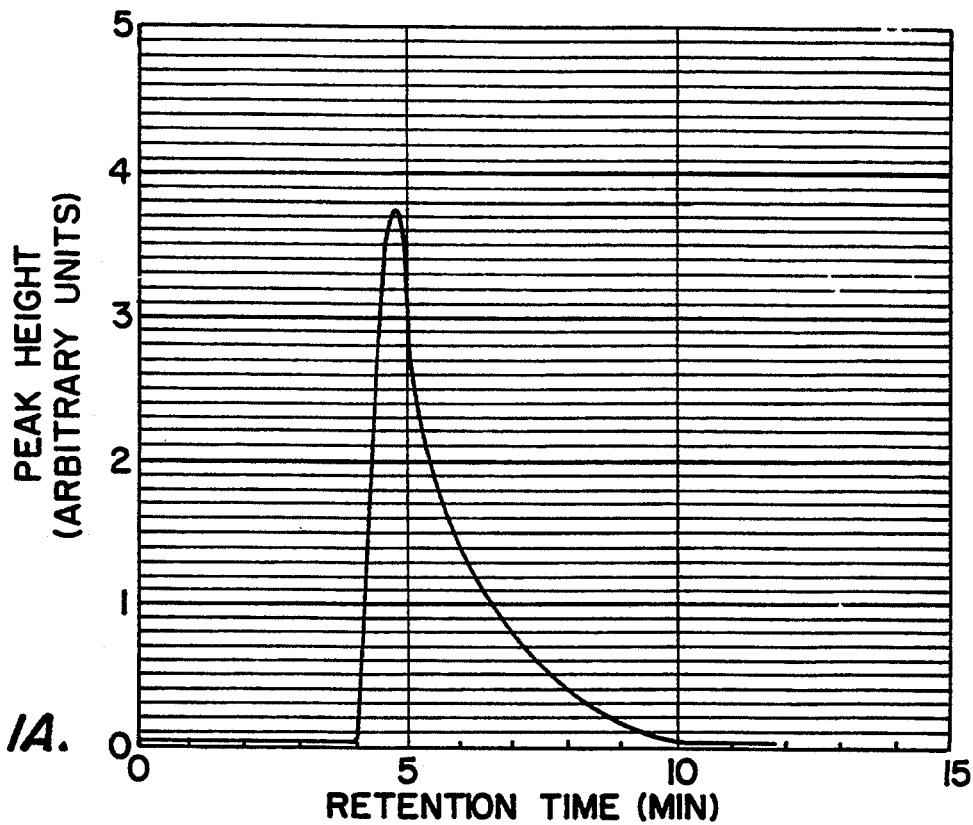
Figure 1B:
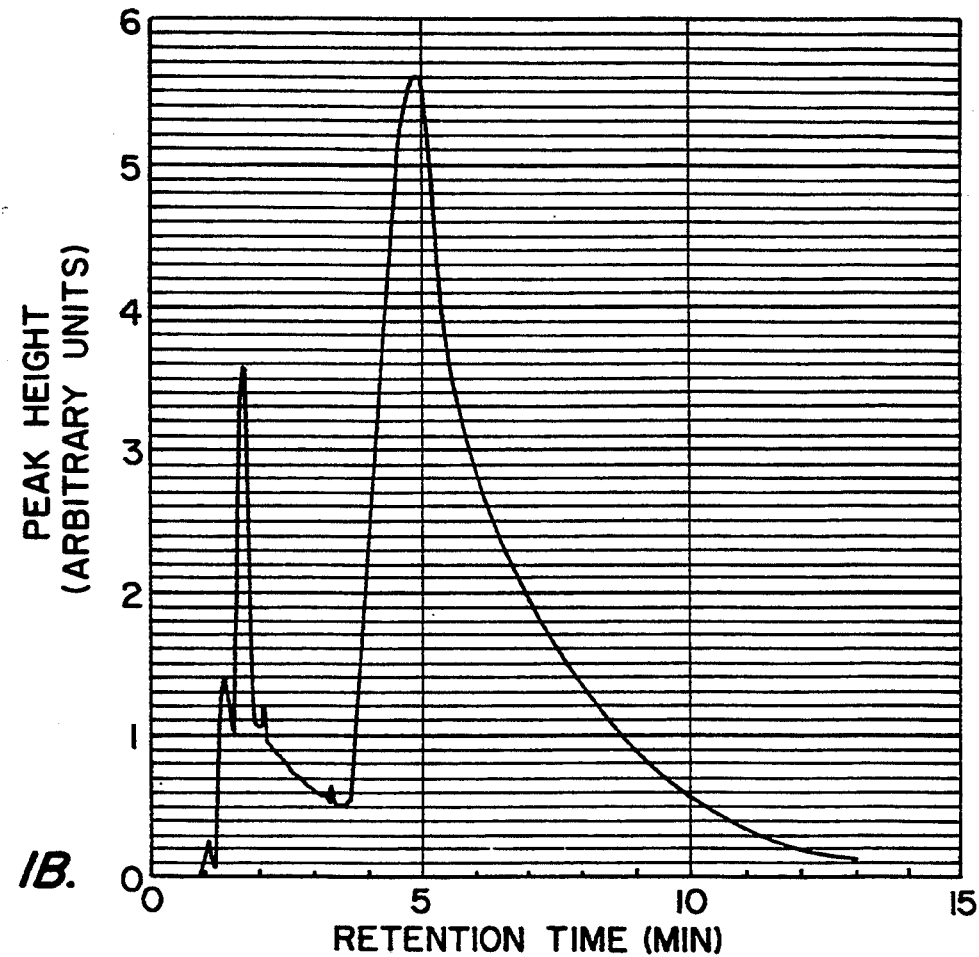
Figure 2:
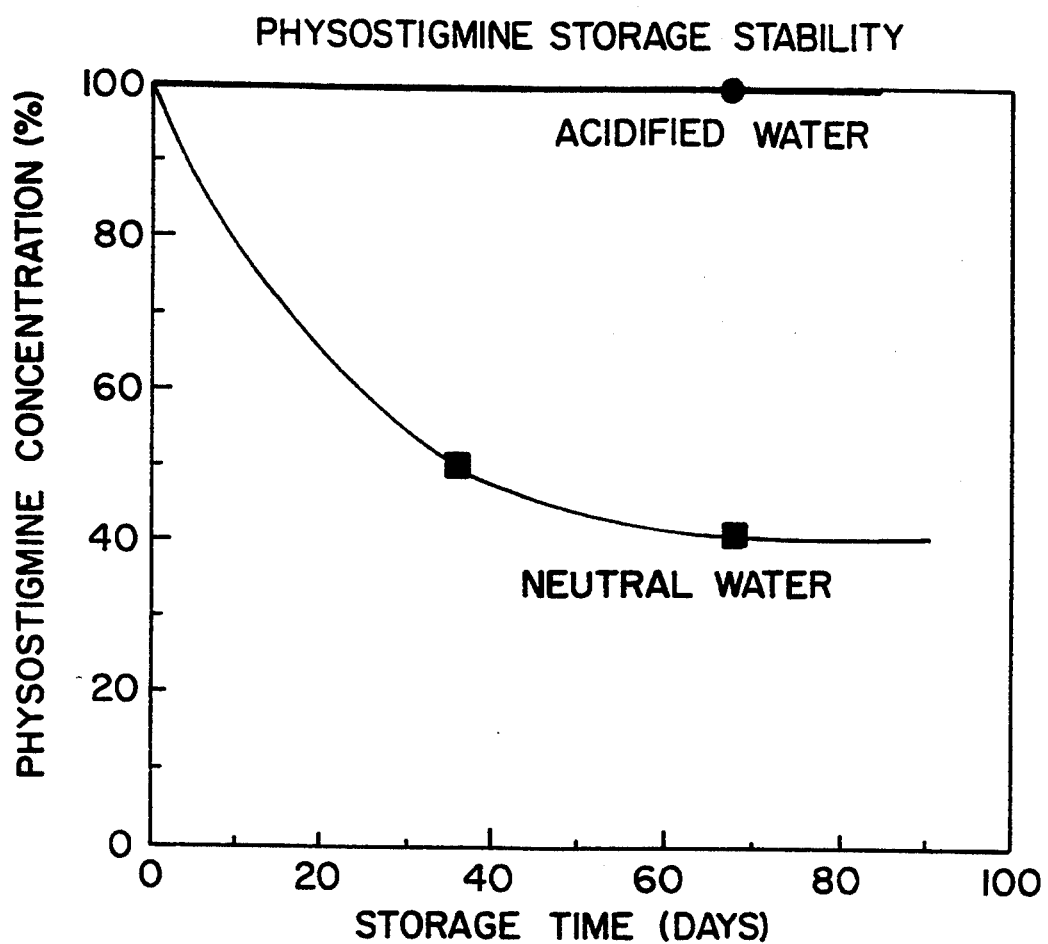

Physostigmine free base is known to be hydrolytically and oxidatively unstable. It has been discovered that when physostigmine free base is contained in a polymer matrix, its stability is markedly increased. A number of techniques may be used to obtain a drug in polymer matrix, including extrusion of blends of polymer and drug (where temperature and shear stability permit), powder compaction, solution methods and the like. In a most elementary embodiment, preparation of a drug loaded matrix is achieved by first dissolving both physostigmine free base and a polymer in an appropriate solvent followed by solution casting. When a clear solution is obtained, the preparation can be cast onto a protective backing by any of the known techniques for casting solvent based polymer films, and the solvent allowed to evaporate. After evaporation, a thin adhesive film is cast onto the matrix, or double-sided medical adhesive tape is attached. The adhesive is covered by a release liner, and patches are cut out by punching. The finished patches may be heat sealed into foil pouches, and stored until needed. The physostigmine free base matrix comprises solid physostigmine free base dispersed in a polymer matrix. The inventors offer the following interpretation of the observed phenomenon for the purposes of explanation without intending to be bound. Since the degradation of physostigmine like compounds require reaction with water and oxygen, polymers with low moisture absorption and low oxygen and moisture transmission prevent degradation by exclusion of an essential reagent for the degradation reaction. Preferably, the polymer should have moisture absorption of less than 5 wt % at 100% relative humidity at 20° C. In order to prevent premature degradation caused by processing and not the result of polymer matrix control, oxygen and moisture should be excluded during the processing of the free base into the finished patch including thorough drying of the polymer before use, conducting the manufacturing operations under and inert atmosphere and sealing the finished patches under an inert atmosphere. One of the preferred polymers is of the polyurethane type. Polyurethanes are usually synthesized using polyisocyanates (hard segment) and polyols (soft segment) of various types. Many of the physical and chemical properties of a polyurethane are determined by the ratio of hard to soft segments as well as the choice of polyol and polyisocyanate reactants. Linear polyurethanes are typically made by the prepolymer route, reacting a hydroxy-terminated compound with a diisocyanate according to the reaction:

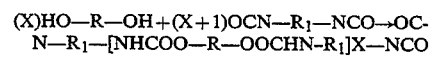

where R is a polyether, polyester, polycarbonate or hydrocarbon.

The product of this reaction is an isocyanate terminated prepolymer. This prepolymer is then further reacted (two shot process) with a lower molecular weight diol (chain extender) such as 1,4-butane diol to produce linear, thermoplastic and solvent soluble elastomers. Alternatively, all the reactants can be combined in a single step (one shot process) to produce the desired product. Polyether soft segmented polyurethanes have better hydrolysis resistance than polyester based polyurethanes but have less oxidative resistance and lower tensile strength; polycarbonate based soft segmented polyurethanes normally occupy a middle ground in physical and chemical properties between the polyether and polyester types. Hydrocarbon based polyols are available and can be used to prepare polyurethanes with superior oxidative and hydrolysis resistance. Aromatic, aliphatic and alicyclic polyisocyanates offer differing degrees of ultra-violet and moisture resistance biocompatibility. Thus, one of ordinary skill in the art of polyurethane synthesis can select appropriate monomers for synthesis to overcome specific application problems. Polyether, polycarbonate and hydrocarbon type polyurethanes are preferred for biomedical use, because, in general, they are more inert than polyester types. Polyurethane polymers are available in grades approved for medical use from Dow Chemical, Midland, Mich. under the trade name Pellethane ™ 2363 and from Thermedics Corporation, Woburn, Massa. under the name of Teccoflex ™ EG-80A and Teccoflex ™ EG-60D. Different hardnesses are available; the softer grades are generally preferred in the context of the present invention, because they are easier to dissolve.

Other polymers that can be used as the polymer matrix material include ethylene vinyl acetate copolymers. These polymers are commercially available (Elvax ®, DuPont Corporation; Ultrathene ®, USI Chemicals, etc.) in a wide variety of grades from 2% to more than 50% vinyl acetate content. Generally, the permeability of the polymer is increased with increasing vinyl acetate content, see Controlled Release of Biologically Active Agents, Baker, R. W., John Wiley & Sons, pp 161-165. Thus, by choosing the appropriate vinyl acetate content and film thickness, an appropriate release characteristic may be obtained. Other useful matrix materials include polyether polyamide block copolymers such as those available from Atochem Inc. under the trade name Pebax ®. Also useful are silicone based polymers of the types available from Dow Corning, General Electric, etc. In general, rubbery polymers are preferred for this application, although glassy polymers such as polyvinyl chloride or ethyl cellulose could be used if supplied as plasticized by the drug or an added pharmacologically acceptable plasticizer such as dioctyl phthalate, polyethyleneglycol, butyl sebacate or the like. The patch may be assembled by any of the techniques known in the art for laminating patches. Typically the first step in preparation of the patch is to prepare a solution of the polymer matrix material. Solvents that may be used to dissolve polyurethane include tetrahydrofuran (THF), Fischer Scientific, Springfield, N.J., dimethylsulfoxide (DMSO), and dimethylformamide (DMF). Tetrahydrofuran is the preferred solvent, because it has been approved for use with medical materials so long as the residue remaining in the material after drying does not exceed 1.5%. Typically the percentage by weight of polyurethane in the solution will be in the range 5% to about 35%, depending on the solvent and the polyurethane grade. Using THF, it is possible to prepare casting solutions with relatively high concentrations, typically around 20 to 25%, of a soft grade polyurethane. The harder grades are more difficult to dissolve. It is usually desirable to make the concentration of polyurethane as high as possible. The solution as cast is closer in thickness to the finished film. Also, concentrated solutions are more viscous, and it has been found that, in general, better containment of physostigmine free base is achieved with films cast from viscous solutions. Solid physostigmine free base is added to the polymer solution, and the mixture is stirred until complete solution is achieved. The percentage of physostigmine free base in the solution may be varied according to the desired loading of the finished matrix. The physostigmine free base content of the finished matrix may vary widely, from around 3% to about 30%. Loading above 30% may be achieved, but because of the potency and toxicity of physostigmine, highly concentrated matrices do not offer advantages that outweigh the hazards associated with potential for accidentally overdosing physostigmine.

Physostigmine free base in polyurethane was chosen as a model compound for the examples given, but one of ordinary skill in the art can apply the general principles and methods to other analogous chemicals.

EXAMPLE 1

Stability of Physostigmine Free Base in Aqueous Solution

Relative stability of physostigmine free base in neutral or alkaline solution was determined as follows. Methanolic solution of physostigmine free base was acidified with a few drops of hydrochloric acid to lower the pH to about 3-6. Aliquots of this solution were analyzed immediately and after one or two hours when the solution became pink due to accumulation of the degradation product rubreserine. Analysis was performed using HPLC Nova Pak 4-C18 column and a mobile phase consisting of:

348.0 g Water
650.0 g Methanol
12.0 g Citric Acid
0.63 g 85% Phosphorous Acid
0.96 g Sodium pentasulphonate

BRIEF DESCRIPTION OF THE DRAWINGS

The chromatogram of physostigmine free base immediately before significant degradation is shown in FIG. 1*a*, the appearance of degradation products of the pink solution that appear after one or two hours is shown in FIG. 1*b*.

In the same manner, stability of physostigmine free base in neutral or slightly acidified water was determined and is shown in FIG. 2. At room temperature, pH 3, the drug is more stable, and slightly pink; however, the drug in neutral solution degrades rapidly with more than half of the initial drug gone within 30 days under the same storage conditions. Repetition of these experiments using ethanol and isopropyl myristate as solvents showed the rate of degradation to be slower than with unbuffered water but faster than with acidified water. In ethanol solution, 5% of the physostigmine free base was lost after 7 days and 10% after 27 days. At this rate of degradation, a patch would have lost 72% of its active ingredient in one year and 92% in two years.

EXAMPLE 2

Stability of Physostigmine Free Base in Polymer Matrix

Increased stability of physostigmine free base in polymer matrices over solutions is shown in the following experiments. Patches containing physostigmine free base in a polymer matrix were prepared by dissolving 18 g of a polyether based polyurethane produced by Dow under the name Pellethane TM grade 2363-80AE, 2.0 g physostigmine free base and 2.0 g isopropyl myristate in 80 g THF. The solution was allowed to stand until clear. A second identical lot of polymer/drug solution was prepared containing 0.02 g of acetyl cystine. Clear solutions were cast onto the reverse side of a polyester-based release liner available from 3M Company of Minneapolis under the trade name Scotch TM 1002. After evaporation of the THF solvent, the liquid cast film of 2000 μm produced a dry matrix film 200–230 μm thick. Patches with an area of 7.9 $cm^2$ were cut from these laminated structures, packaged in polyethylene foil pouches and stored at room temperature and at 45° C.

Three patches from each lot were tested for physostigmine free base content immediately after manufacture and after 7 and 25 days of storage at room temperature and at 45° C. Once the backing was removed from the patch, the drug-containing film was weighed and then dissolved in 25 g of THF, followed by dilution with 25 g on methanol. Precipitated Pellethane TM was filtered from the solution before injection into the HPLC. Average amounts of physostigmine free base recovered from the patches, with and without acetyl cysteine, are given in Table I. Theoretical drug loadings were 17.2 and 16.2 mg for the stabilized and unstabilized patches, respectively. Scatter in the weight data can be attributed to variation in film weights and analytical errors amounting to as much as ±10%.

TABLE I

Stability of Physostigmine Free Base Patches with and without Preservatives (n = 3)

| Storage Time (days) | Weight of Physostigmine free base Recovered (mg): No Preservative, Room Temperature | No Preservative, 45° C. | With Preservative, Room Temperature | With Preservative, 45° C. |
|---|---|---|---|---|
| Theoretical Loading | 17.2 | 17.2 | 16.2 | 16.2 |
| 0 | 15.0 | 15.0 | 15.1 | 15.1 |
| 7 | 16.5 | 16.8 | 17.3 | 16.8 |
| 25 | 16.8 | 18.5 | 16.8 | 16.8 |

Within the limits of error, there was no measurable physostigmine free base loss during these tests either at room temperature or at 45° C. Patches stored for 25 days at 45° C. appeared slightly discolored; however, no additional peaks were observed in the HPLC analysis of these patches.

EXAMPLE 3

In Vivo Test of Physostigmine Free Base Patches

Pellethane ™ 2363-80AE (24.4 g) was added to a solution of 101.3 g of THF containing 2.903 g of physostigmine free base and 2.951 g of isopropyl myristate and stirred until a clear solution was formed. After evaporation of the THF solvent, the liquid cast film of 2000 μm produced a dry matrix film 180–230 μm thick. A solution of Avery adhesive 460, containing 10 wt % isopropyl myristate was cast on the drug/polymer matrix film to produce an adhesive layer approximately 801 μm thick. The film was finally overlaid with a release liner film 1022 available from 3M Company and patches with an area of 7.92 cm² were cut from the laminated structure. These patches were weighed, heat sealed into polyethylene-foil pouches and stored until use.

The patches were then placed on the skin of rabbits from which the hair had been carefully clipped, after 23 hours, the patches were removed and the in vivo skin fluxes determined and summarized in Table II.

TABLE II

Rabbit Test Results

| Patch | Patch Weight (mg) | Film Weight (mg) | Calculated Drug Load (mg) | Drug Remaining in Patch* (mg) | Drug Delivered ΔMass (mg) | Drug Delivered ΔMass (%) | ΔMass time (mg/hr) | Average Total Delivery Flux (μg/cm² · hr) |
|---|---|---|---|---|---|---|---|---|
| 1 | 408 | 229 | 22.0 | 6.8 | 15.2 | 69 | 0.66 | 83 |
| 2 | 412 | 233 | 22.4 | 7.4 | 15.0 | 67 | 0.65 | 82 |
| 3 | 396 | 217 | 20.8 | 6.8 | 14.0 | 67 | 0.61 | 77 |
| 4 | 417 | 238 | 22.8 | 7.1 | 15.7 | 69 | 0.68 | 86 |
| 5 | 359 | 180 | 17.2 | 5.2 | 12.0 | 70 | 0.52 | 66 |
| 6 | 415 | 236 | 22.7 | 6.7 | 16.0 | 70 | 0.70 | 88 |
| 7 | 367 | 188 | 18.0 | 5.2 | 12.8 | 71 | 0.56 | 71 |
| 8 | 393 | 214 | 20.5 | 6.2 | 14.3 | 70 | 0.62 | 78 |
| 9 | 390 | 211 | 20.2 | 6.5 | 13.7 | 68 | 0.60 | 75 |
| 10 | 411 | 232 | 22.3 | 7.1 | 15.2 | 68 | 0.66 | 83 |
| 11 | 371 | 192 | 18.4 | 5.7 | 12.7 | 69 | 0.55 | 70 |
| 12 | 353 | 174 | 16.7 | 4.9 | 11.8 | 71 | 0.51 | 64 |
| Average | 391 | 212 | 20.3 | 6.3 | 14.0 | 69 | 0.61 | 77 |
| Std. Dev. | 22 | 22 | 2.1 | 0.8 | 1.4 | 1 | 0.06 | 8 |
| % CV | 5.6 | 10.4 | 10.5 | 12.9 | 9.8 | 1.9 | 9.8 | 9.8 |

*Measured by HPLC.
Average weight of backing, adhesive, and liner = 0.179 g
Patch area = 7.9 cm²

Over the 23 hour period the average total drug flux to the rabbits was 0.77±8 μg/cm²·h with approximately 70% of the drug delivered. Average Physostigmine free base flux was 160 μg/cm²·h.

We claim:

1. A process for increasing the storage stability of physostigmine comprised of:
   a. dissolving a polymer having a water absorption of less than 5 wt % at 100% relative humidity at 20° C. and physostigmine in a solvent to form a drug and polymer solution;
   b. casting said drug and polymer solution to form a cast solution;
   c. removing the solvent from said cast solution to form a matrix; and
   d. recovering said matrix.

2. The process according to claim 1 where an enhancer solution is added to the drug and polymer solution of step a.

3. The process according to claim 1 where said polymer is a polyurethane.

4. The process according to claim 1 where said polymer is a polyether polyuethane.

5. The process according to claim 1 wherein said polymer is a silicone polymer.

6. The process according to claim 1 wherein said polymer is an ethylene vinyl acetate copolymer.

* * * * *